United States Patent
Karashima

(10) Patent No.: US 7,917,205 B2
(45) Date of Patent: Mar. 29, 2011

(54) IONTOPHORESIS-BASED MEDICAL DEVICE

(76) Inventor: Nobuyoshi Karashima, Oita (JP)

( * ) Notice: Subject to any disclaimer, the term of this patent is extended or adjusted under 35 U.S.C. 154(b) by 68 days.

(21) Appl. No.: 12/585,106

(22) Filed: Sep. 3, 2009

(65) Prior Publication Data

US 2010/0069823 A1    Mar. 18, 2010

Related U.S. Application Data

(63) Continuation-in-part of application No. 10/800,914, filed on Mar. 16, 2004, now abandoned.

(30) Foreign Application Priority Data

Mar. 20, 2003    (JP) .................................. 2003-078236

(51) Int. Cl.
    *A61N 1/30*    (2006.01)
(52) U.S. Cl. ............................................ 604/20; 433/32
(58) Field of Classification Search .............. 604/19–20, 604/500, 501; 433/32, 80, 82, 215, 224
    See application file for complete search history.

(56) References Cited

U.S. PATENT DOCUMENTS

| | | | | |
|---|---|---|---|---|
| 4,149,533 A | | 4/1979 | Ishikawa et al. ................. 604/20 |
| 4,676,257 A | * | 6/1987 | Halpern ......................... 607/134 |
| 5,601,689 A | | 2/1997 | Sacripante et al. ............... 162/5 |
| 5,730,600 A | * | 3/1998 | Shoher et al. ................. 433/215 |
| 5,944,715 A | | 8/1999 | Goble et al. ..................... 606/41 |
| 6,491,522 B1 | * | 12/2002 | Jensen .......................... 433/215 |
| 6,517,350 B2 | * | 2/2003 | Diasti et al. ................... 433/215 |
| 6,600,950 B1 | | 7/2003 | Tapper ............................ 604/20 |
| 6,635,045 B2 | | 10/2003 | Carey et al. .................... 604/501 |
| 7,040,893 B2 | | 5/2006 | Fischer ........................... 433/80 |
| 2001/0046653 A1 | * | 11/2001 | Legarde ......................... 433/32 |
| 2003/0044755 A1 | | 3/2003 | Jensen .......................... 433/215 |
| 2004/0062744 A1 | * | 4/2004 | Miyamoto et al. ......... 424/78.27 |

FOREIGN PATENT DOCUMENTS

| | | |
|---|---|---|
| JP | 8-98894 A | 4/1996 |
| JP | 8-164212 A | 6/1996 |
| JP | 3049455 U | 3/1998 |
| JP | 2001-293016 A | 10/2001 |

* cited by examiner

*Primary Examiner* — Nicholas D Lucchesi
*Assistant Examiner* — Quynh-Nhu H Vu
(74) *Attorney, Agent, or Firm* — Jordan and Hamburg LLP

(57)    ABSTRACT

An iontophoresis-based medical device includes a positive electrode section, a negative electrode section, a power source supplying an electric current to the positive electrode section and negative electrode section and a controller controlling the current value and conduction time of the electric current, wherein a writing brush is electrically connected to the positive electrode section, and a sponge is electrically connected to the negative electrode section, and the writing brush is formed of a large number of long soft hairs and a large number of short soft hairs such that the writing brush has a columnar shape at a base portion thereof and is gradually tapered toward a tip portion thereof from a middle portion thereof and the tip portion is made extremely fine to form an acute apex thus allowing the apex to touch an affected part in a pinpoint manner.

3 Claims, 7 Drawing Sheets

IONTOPHORESIS-BASED MEDICAL DEVICE

BACKGROUND OF THE INVENTION

1. Field of the Invention

This invention relates to an iontophoresis-based medical device for sterilizing and disinfecting body tissues and, more particularly, to an iontophoresis-based medical device for sterilizing and disinfecting body tissues to treat a part of an animal affected by a pathogen, for example, by using a drug solution permeated into the lesion by means of iontophoresis.

2. Description of the Prior Art

A conventional iontophoresis-based medical device for sterilizing and treating a tooth infected with a pathogenic organism by iontophoresis is known, for example, as the device claimed in the Patent literature 1.

The conventional iontophoresis-based medical device was provided with an electric circuit having a voltage generator and a current-supplied application apparatus, a positive electrode section and a negative electrode section, wherein the positive electrode section was provided needle-shaped and deeply inserted into a tooth duct and the negative electrode section was directly attached to a part of a patient body, and the voltage generator fed a direct current and the electric circuit was provided with an apparatus to maintain a constant direct current while an impedance of the electric circuit varied, and the impedance was determined depending on a body part of a patient through which a current passed.

In sterilizing and treating a tooth, a drug solution applied to the needle-shaped positive electrode section was inserted into a tooth duct, and the negative electrode section was attached to a part of a patient (for example, the wrist) to effect electric conduction. This process made it possible to provide a closed electric circuit among the power source, the electric circuit, the positive and negative electrode sections, the tooth and the part of the patient, thereby allowing permeation of the drug solution deeply into the tooth duct by iontophoresis to sterilize and treat the lesion.

[Patent literature 1] Japanese Published Unexamined Patent Application No. 2001-293016 (FIG. 1 on page 1)

Drug solutions including halogen elements such as fluorine, iodine or chloride were used as those permeated into a lesion in treatment by conventional iontophoresis-based medical devices. Drug solutions including metal elements such as silver or zinc were also used.

However, as described above, the conventional iontophoresis-based medical device was provided with a needle-shaped positive electrode section directly contacting with a lesion. Such a shape of the positive electrode section provided a lesion with a limited quantity of a drug solution at one time. Therefore, in order to attain a predetermined therapeutic effect, it was necessary to discontinue treatment to apply the drug solution to the positive electrode section several times, thus resulting in a prolonged treatment.

Further, according to the conventional iontophoresis-based medical device, the negative electrode section was designed to be attached to apart of the body largely apart from the lesion, for example, the wrist. Thus, the negative electrode section was a great distance from the positive electrode section and unable to give a sufficient iontophoresis-based therapeutic effect to the lesion.

In addition, the negative electrode section was required to have a dimension sufficient to be worn on the wrist. Further, in order to detachably attach the negative electrode section to the wrist conveniently, such an attachable and detachable structure as a spring-mounted supporting structure or belt-fastening structure was needed, entailing troublesome wearing and removing processes. Consequently, it was difficult to handle these electrode sections at the time of treatment.

In addition, conventional drug solutions were restricted to either drug solutions containing halogen elements or those containing metallic elements. Iontophoresis methods using these drug solutions were low in sterilization effect and none of them were able to attain a sufficient sterilization and treatment.

SUMMARY OF THE INVENTION

Under these circumstances, the inventor discovered that current level necessary for treatment could be conducted even at a lower voltage by making a positive electrode and a negative electrode approximate to each other as much as possible to clip a lesion so that a current-conducting circuit was restricted to a narrow area and lowering an electric resistance in the circuit.

Finding that such arrangement was able to attain iontophoresis wherein drug ions were supplied only to a necessary area of a lesion, thus reducing to the least possible extent development of stimulation, derived adverse effects resulting in permeation of drug ions into cells and tissues other than necessary sites, the inventor completed the present invention. It was also found that use of the device at the lowest possible voltage was able to suppress electric stimulation to nerves.

An object of the invention is to provide an iontophoresis-based medical device which is able to increase a quantity of the drug solution supplied to a lesion, thereby reducing treatment time, improve the therapeutic effect of the lesion and also improve the handling of the positive electrode section and the negative electrode section during the treatment.

Further, this invention is to provide an iontophoresis-based medical device that is able to give treatment suitable for a position and condition of the lesion.

An additional object of the invention is to provide an iontophoresis-based medical device that is able to give a high sterilization effect to a lesion at a reduced cost through utilization of iontophoresis.

A further object of the invention is to provide an iontophoresis-based medical device that is able to provide a highly safe sterilization treatment.

According to one aspect of the present invention, there is provided an iontophoresis-based medical device which includes: a device body having a positive electrode connecting terminal and a negative electrode connecting terminal; a stick-shaped positive electrode section connected to the positive electrode connecting terminal and capable of retaining a drug solution in which an anti-microbial drug solution is dissolved therein; a stick-shaped negative electrode section connected to the negative electrode connecting terminal and capable of retaining a solution increasing the conductivity therein; and an electric circuit connecting the positive electrode section and the negative electrode section respectively with a power source, wherein the device body has a rectangular device box on which the positive electrode connecting terminal, the negative electrode connecting terminal, a voltage adjusting knob, an output changeover switch for changing over continuous conduction and a timer control, an electric conduction time knob for changing an electric conduction time, and a timer start switch are mounted, the positive electrode section is connected to the positive electrode connecting terminal via a lead line, and the negative electrode section is connected to the negative electrode connecting terminal via a lead line, a writing brush is electrically connected to a distal end of the positive electrode section, and a sponge is electrically connected to a distal end of the negative electrode section, the writing brush is impregnated with an aqueous solution of a cationic surface active agent and the sponge is impregnated with a sodium chloride solution, the writing brush is formed of a large number of blended hairs consisting of a large number of long soft hairs and a large number of short soft hairs such that the writing brush has a columnar shape at a base portion thereof and is gradually tapered toward a tip portion thereof from a middle portion thereof and the tip portion is made extremely fine to form an acute apex thus allowing the apex to touch an affected part in a pinpoint manner, and the base portion of the writing brush formed of the blended hairs is made hard and the middle portion and the tip portion of the writing brush are made soft so that air pockets are formed in the large number of hairs so as to absorb and store a drug solution in the middle portion and the tip portion of the writing brush through capillarity, whereby conductivity of electricity to the writing brush at the positive electrode section is enhanced thus easily generating iontophoresis.

According to this invention, for example, an operator allows a writing brush which constitutes a drug solution retainer in which a drug solution is retained to come into contact with a lesion (part of the body tissue), with a positive electrode section held with one hand, and also allows a sponge which constitutes a solution retainer in which a solution is retained to come into contact with the lesion or a part of the body around the lesion (for example, a site as close as possible to the lesion), with a negative electrode section held with the other hand, thereby providing a closed electric circuit among a power source, the electrode sections and the lesion (including the site around the lesion). When a low electric current is conducted from the power source, in this condition, iontophoresis takes place, allowing the drug solution to permeate deeply into the lesion. At this time, a large quantity of the drug solution retained by the writing brush which constitutes the drug solution retainer is present in the positive electrode section and a large quantity of the solution retained by the sponge which constitutes the solution retainer is present in the negative electrode section, thereby further increasing the iontophoresis effect than that obtained by a conventional method. Therefore, a lesion can be treated including that at a deep site, the treatment of which is otherwise difficult by mere application of a drug solution.

Particularly, the writing brush is formed of a large number of blended hairs consisting of a large number of long soft hairs and a large number of short soft hairs such that the writing brush has a columnar shape at a base portion thereof and is gradually tapered toward a tip portion thereof from a middle portion thereof and the tip portion is sharpened to form an acute apex thus allowing the apex to touch an affected part in a pinpoint manner. The base portion of the writing brush formed of the blended hairs is made hard and the middle portion and the tip portion of the writing brush is made soft such that air pockets are formed among the large number of hairs so as to absorb and store a drug solution in the middle portion and the tip portion of the writing brush by making use of capillarity. Further, 5 to 20% of the long soft hairs are formed of carbon fibers having the same diameter and the same length as the long soft hairs with respect to 100% of the long soft hairs thus forming the blended hairs consisting of the long soft hairs, the short soft hairs and the carbon fibers. Due to such constitution, conductivity of electricity to the writing brush at the positive electrode section is enhanced thus easily generating iontophoresis.

Further, the drug solution retainer of the positive electrode section which is configured to retain a large quantity of the drug solution and the solution retainer of the negative electrode section which is configured to retain a large quantity of the solution are made of different materials from each other such that the drug solution retainer is made of the writing brush and the drug solution is made of the sponge. Accordingly, while the drug solution retainer made of writing brush can touch an affected part in a pinpoint manner, the solution retainer made of sponge can ensure a wide contact area with the gingiva or the like and hence, it is possible establish the more reliable closed electric circuit among the power source, the electric circuit, the positive and negative electrode sections, the tooth and the part of the patient, thereby further enhancing the permeation of the drug solution deeply into the tooth duct by iontophoresis to sterilize and treat the lesion.

DETAILED DESCRIPTION OF THE PREFERRED EMBODIMENT

Figure 1:
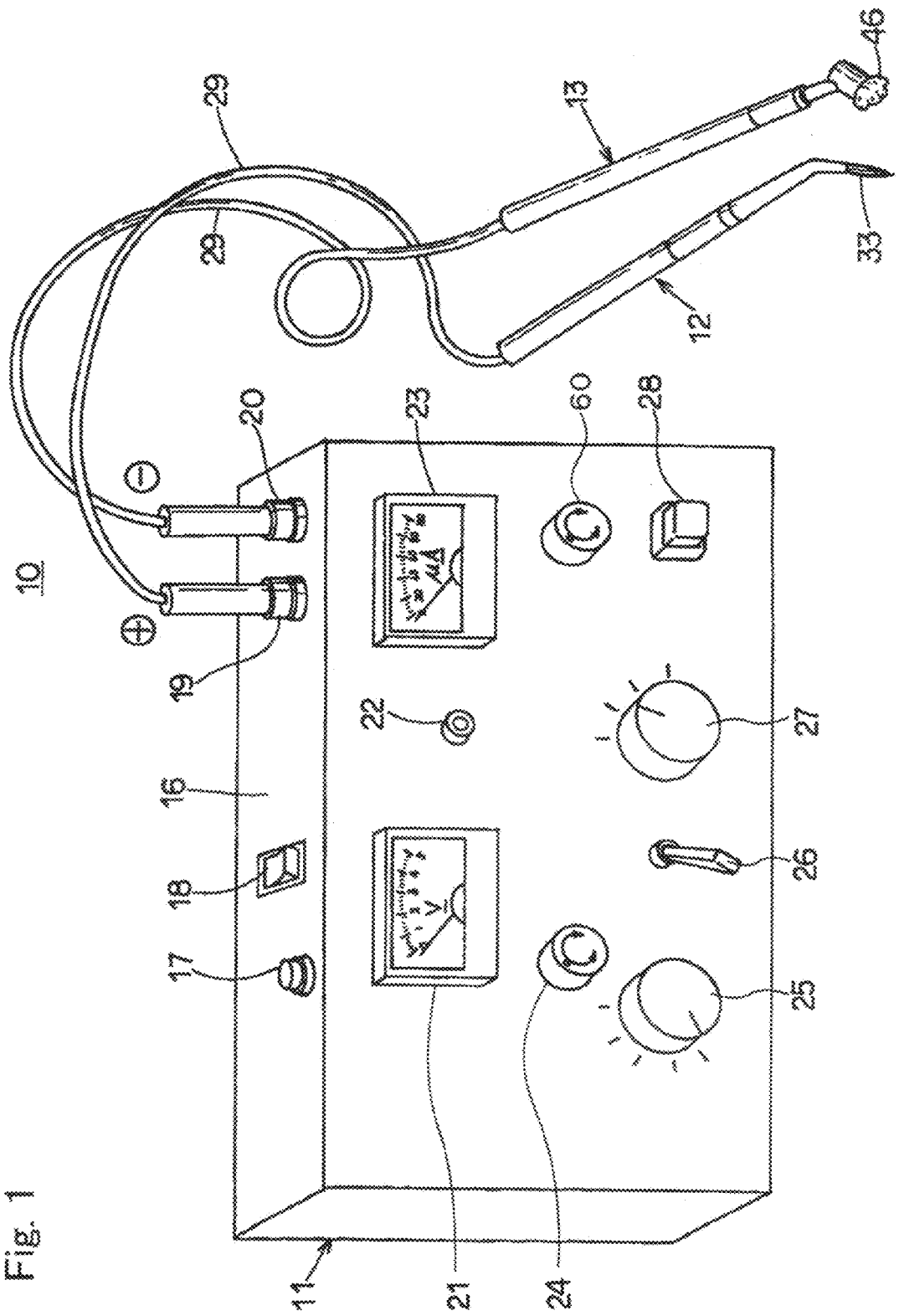
FIG. 1 is an overall perspective view of the iontophoresis-based medical device according to one embodiment of the present invention.

The embodiment of the present invention will be explained hereinafter by referring to the drawings.

Figure 4A:
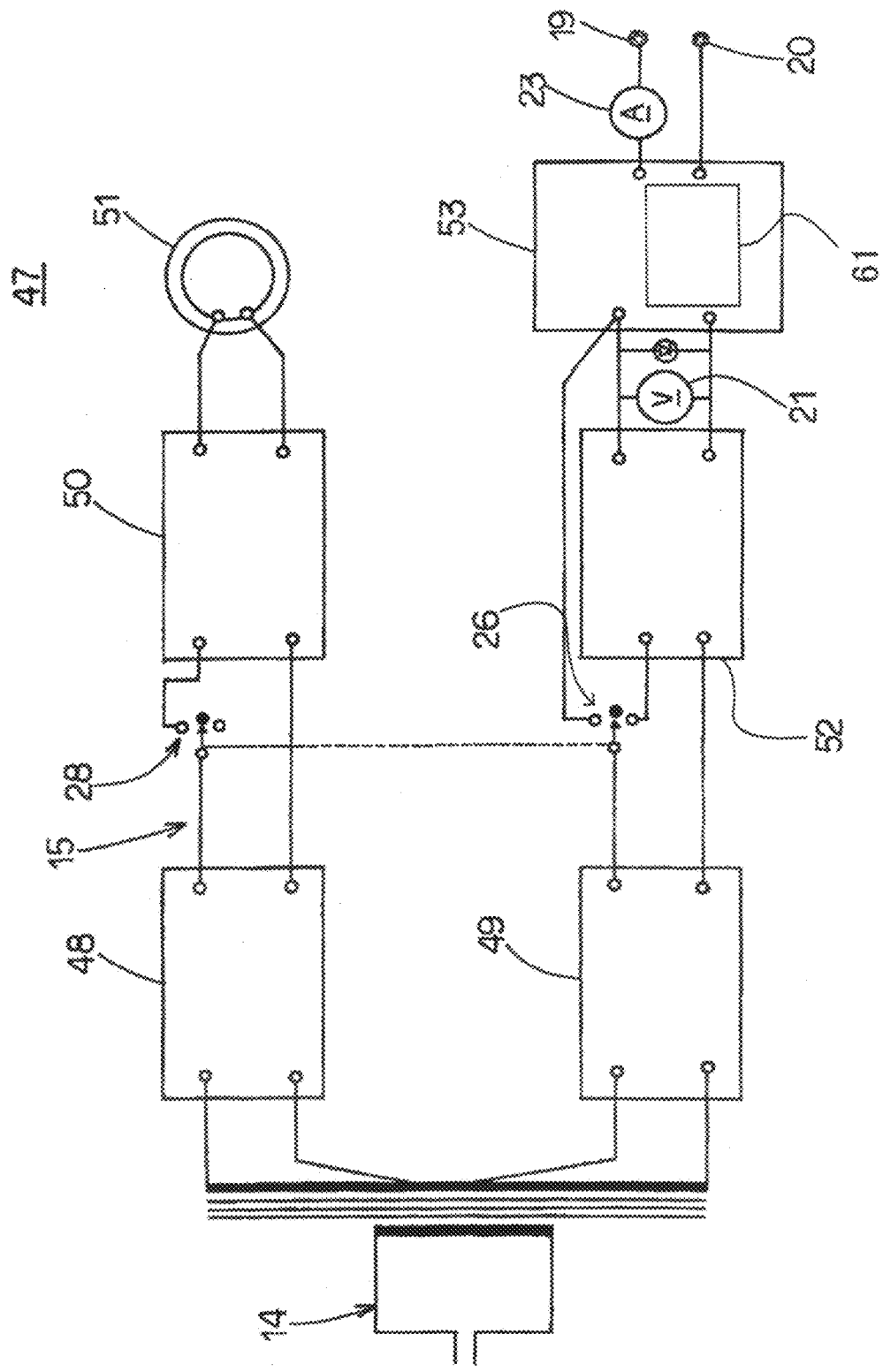
FIG. 4 is an electric circuit diagram of the controller of the iontophoresis-based medical device according to one embodiment of the present invention.

In FIG. 1 and FIG. 4, 10 denotes an iontophoresis-based medical device according to one embodiment of the present invention, the iontophoresis-based medical device 10 comprises a device body 11, a stick-shaped positive electrode section 12 connected to the device body 11 and capable of retaining a drug solution in which an anti-microbial drug solution is dissolved, a stick-shaped negative electrode section 13 connected to the device body 11 and capable of retaining a solution increasing the conductivity, an electric circuit 15 connecting the positive electrode section 12 and the negative electrode section 13 respectively with a power source 14, and a polarity inverting circuit 61 which is connected to the electric circuit 15 so as to invert polarity of a voltage applied to a positive electrode connecting terminal 19 to which the positive electrode section 12 is connected and polarity of a voltage applied to a negative electrode connecting terminal 20 to which the negative electrode section 13 is connected at a predetermined time rate.

The device body 11 is provided with a rectangular device box 16. On the top of the device box 16, mounted are a fuse 17, a power switch 18, a positive electrode connecting terminal 19 and a negative electrode connecting terminal 20. Further, on the front plate of the device box 16, mounted are a voltage indicator 21, a pilot lamp 22, an ampere meter 23, a voltage adjusting knob 24, a buzzer knob 25 which changes the buzzer (alarm) sounding time and is built into the device box 16, an output switch 26 for changing from continuous conduction to timer control or vice versa, an electric conduction time knob 27 for changing the electric conduction time, a timer start switch 28, and a polarity inversion rate adjustment knob 60 which adjusts a polarity inversion time rate.

The positive electrode connecting terminal 19 is connected through a lead wire 29 to the positive electrode section 12. Further, the negative electrode connecting terminal 20 is connected through a lead wire 29 to the negative electrode section 13. The power source 14 is a 100V alternate current for home use, which is converted into direct current (6V) through a converter upon usage.

The buzzer knob 25 is a knob for adjusting intervals of sounding of the buzzer indicating a passage of predetermined electric conduction time (sterilization and treatment time). Intervals of the buzzer can be arbitrarily selected from four different intervals of 2 seconds, 4 seconds, 6 seconds and 8 seconds. It is also possible to make such an arrangement that the alarm lamp can be made to flash according to the sound of the buzzer.

Next, electric conduction time knob 27 is a knob for adjusting intervals of switching between conduction and discontinued conduction. The conduction and discontinued conduction can be arbitrarily selected from three intervals of 2 seconds, 3 seconds and 6 seconds.

Then, an explanation will be made for the positive electrode section 12 and the negative electrode section 13, by referring to FIG. 2 and FIG. 3.

Figure 2A:
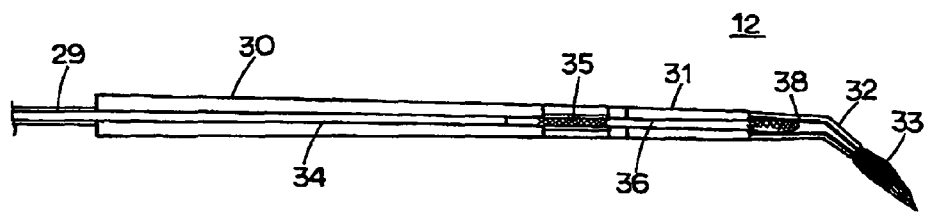
FIG. 2(a) is a sectional view of the positive electrode section used in the iontophoresis-based medical device according to one embodiment of the present invention.
Figure 2B:
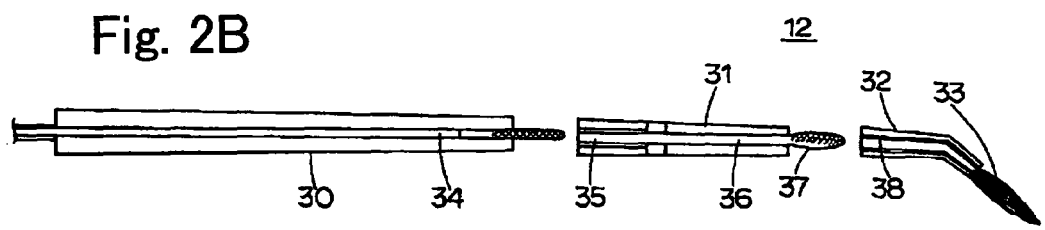
FIG. 2(b) is an exploded sectional view of the positive electrode section used in the iontophoresis-based medical device according to one embodiment of the present invention.

The positive electrode section 12 shown in FIG. 2 is mainly provided with a handle 30 which is an insulative plastic-made narrow tube, an intermediate part 31 which is an insulative plastic-made narrow tube connected to the tip end of the handle 30 in an attachable and detachable manner and having about half the length of the handle 30, a brass-made mouth piece 32 connected to the tip end of the intermediate part 31 in an attachable and detachable manner, the end of which is bent about 45 degrees, and an animal hair-fabricated writing brush or writing brush (drug solution retainer) 33 fixed at the tip end of the mouth piece 32.

A nickel silver wire 34 connected to a lead wire 29 extended from said positive electrode connecting terminal 19 is inserted into a duct of the handle 30 which is a pipe having a circular cross section. The tip end of the nickel silver wire 34 protrudes from the end surface of the handle 30. A narrow nickel silver tube 35 is fitted into a duct on the proximal side of the intermediate part 31. A nickel silver wire 36 connected with a nickel silver tube 35 is inserted into the other duct of the intermediate part 31. When the handle 30 is connected with the intermediate part 31, the tip end of the nickel silver wire 34 on the side of the handle 30 is attached to the proximal side of the nickel silver tube 35. A gold-plated 37 tip end of the nickel silver wire 36 protrudes from the end surface of the intermediate part 31. An inner wall of the duct of the mouth piece 32 is provided with gold plate 38 contacting with said writing brush 33 on the tip end.

The writing brush 33 is formed of a large number of blended hairs consisting of a large number of long soft hairs made of a synthetic resin such as polyester or polypropylene, for example, and a large number of short soft hairs made of a synthetic resin such as polyester or polypropylene, for example, such that the writing brush has a columnar shape at a base portion thereof and is gradually tapered toward a tip portion thereof from a middle portion thereof and the tip portion is made extremely fine to form an acute apex thus allowing the apex to touch an affected part in a pinpoint manner, The base portion of the writing brush formed of the blended hairs is made hard and the middle portion and the tip portion of the writing brush are made soft so that air pockets are formed in the large number of hairs so as to absorb and store a drug solution in the middle portion and the tip portion of the writing brush through capillarity.

A thin paste is applied to a peripheral surface of mixed hairs and a portion of the thin paste is impregnated into minute gaps defined among the hairs so as to shape up a base portion, a middle portion and a distal portion of the writing brush 33.

A total length of the writing brush 33 is preferably set to 20 mm to 50 mm, a diameter of a cylindrical portion of the writing brush 33 made of mixed hairs is preferably set to 7 mm to 15 mm, and the total number of hairs is preferably set to 500 to 1000.

It is particularly preferable that 5 to 20% of the long soft hairs are formed of carbon fibers having the same diameter and the same length as the remaining 95 to 80% of long soft hairs made of the synthetic resin such as polyester or polypropylene thus forming the blended hairs consisting of the long soft hairs, the short soft hairs and the carbon fibers, whereby conductivity of electricity to the writing brush 33 at the positive electrode section 12 is enhanced thus easily generating iontophoresis.

A benzalkonium chloride solution is impregnated into the writing brush 33. When the intermediate part 31 is connected with the mouth piece 32, the tip end of a nickel silver wire 36 on the side of the intermediate part 31 is inserted into the proximal part of the mouth piece 32. By connecting the handle 30, the intermediate part 31 and the mouth piece 32, the positive electrode connecting terminal 19 of the device body 11 is electrically connected with the writing brush 33.

Figure 3A:
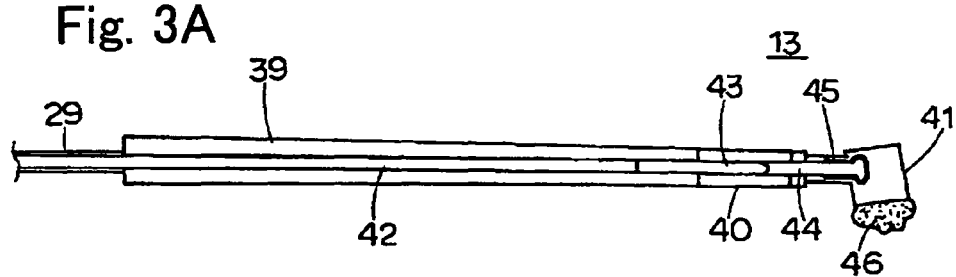
FIG. 3(a) is a sectional view of the negative electrode section used in the iontophoresis-based medical device according to one embodiment of the present invention.
Figure 3B:
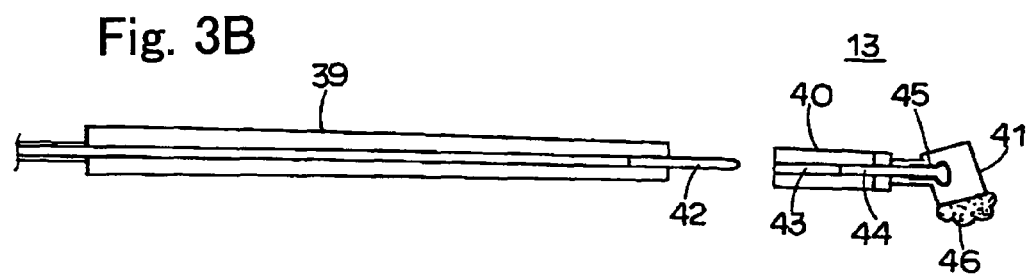
FIG. 3(b) is an exploded sectional view of the negative electrode section used in the iontophoresis-based medical device according to one embodiment of the present invention.

The negative electrode section 13 shown in FIG. 3 is mainly provided with a handle 39 which is an insulative plastic-made narrow tube, an intermediate part 40 which is an insulative plastic-made short and narrow tube connected to the tip end of the handle 39 in an attachable and detachable manner and a short cylindrical head 41 fixed to the tip end of the intermediate part 40.

A nickel silver wire 42 connected to a lead wire 29 extending from said negative electrode connecting terminal 20 is inserted into a duct of the handle 39. The tip end of the nickel silver wire 42 protrudes from the end surface of the handle 39. A narrow nickel silver tube 43 is fitted into a duct on the proximal side of the intermediate part 40, and a nickel silver wire 44 connected with the nickel silver tube 43 is inserted into the other duct of the intermediate part 40. When the intermediate part 40 is connected with the handle 39, the tip end of the nickel silver wire 42 on the side of the handle 39 is attached to the proximal side of the nickel silver tube 43. The nickel silver wire 44 on the side of the intermediate part 40 is gold-plated 45 at the tip end, and extended up to the inside of the cylindrical head 41. The cylindrical head 41 is made with polypropylene and provided with a sponge (solution retainer) 46 on the top of the cylindrical head in an attachable and detachable manner. For increasing the conductivity, 1 to 3% (% by volume) sodium chloride aqueous solution is impregnated into the sponge 46. Thus, connecting the handle 39 with the intermediate part 40 to which the cylindrical head 41 is attached can provide an electric connection of the negative electrode connecting terminal 20 of the device body 11 with the sponge 46.

Now, an explanation will be made for the controller 47 of the iontophoresis-based medical device 10 by referring to FIG. 4.

As shown in FIG. 4, the controller 47 acts to convert a 100V alternate current into a 6V direct current through a rectifier-built constant voltage circuit 48 and also converts it to 0 to 5V direct current through a trans- and rectifier-built constant voltage circuit 49. The constant voltage circuit 48 supplies direct current for an intermittent timer circuit 50 to actuate a buzzer 51. The buzzer 51 is directly connected to the intermittent timer circuit 50. The constant voltage circuit 49 supplies direct current to a timer circuit 52 for conduction. A current limiting circuit 53 is connected to a timer circuit 52. Said positive electrode connecting terminal 19 and the negative electrode connecting terminal 20 are respectively connected to the current limiting circuit 53.

In the inside of the current limiting circuit 53, the polarity inverting circuit 61 is further provided so as to invert polarity of a voltage applied to the positive electrode connecting terminal 19 and polarity of a voltage applied to the negative electrode connecting terminal 20 at a predetermined time rate.

The inversion of the polarities of voltages is performed so as to induce the drug from the positive electrode section towards the gingiva direction by electrophoresis thus removing the foreign materials which are charged with a positive charge in an oral cavity and are also induced onto the gingiva.

That is, when the foreign materials which is charged with the positive charge and is contained in saliva or the like is induced to the negative electrode section 13 and is stacked on the gingiva during the penetration of the drug into the gingiva, the penetration of the drug gradually slows down thus impeding the effective treatment.

Accordingly, an iontophortsis-based medical device 10 of this embodiment inverts polarity of the voltage for a short time and the foreign materials stacked on the gingiva is once induced to the positive electrode section 12 and the foreign materials is removed from the gingiva.

Figure 4B:
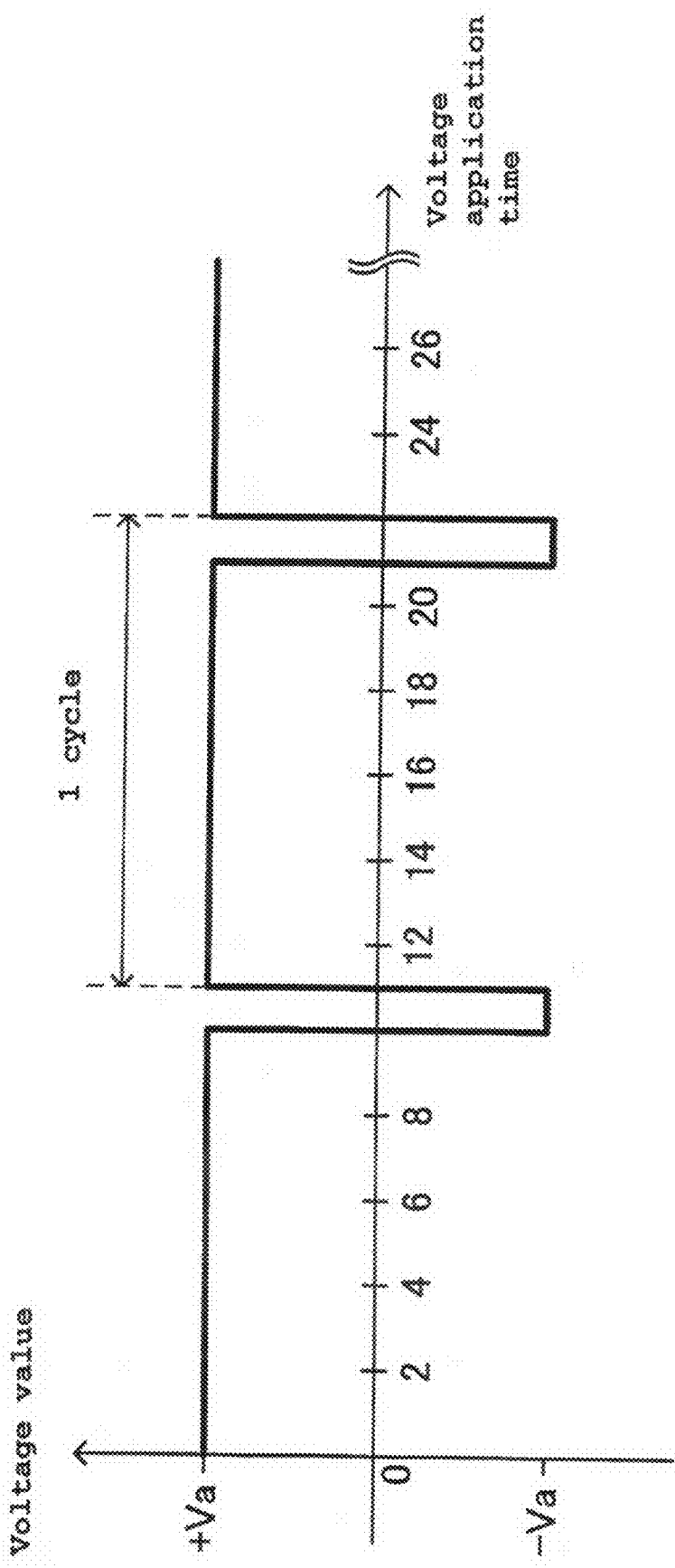
Figure 5:
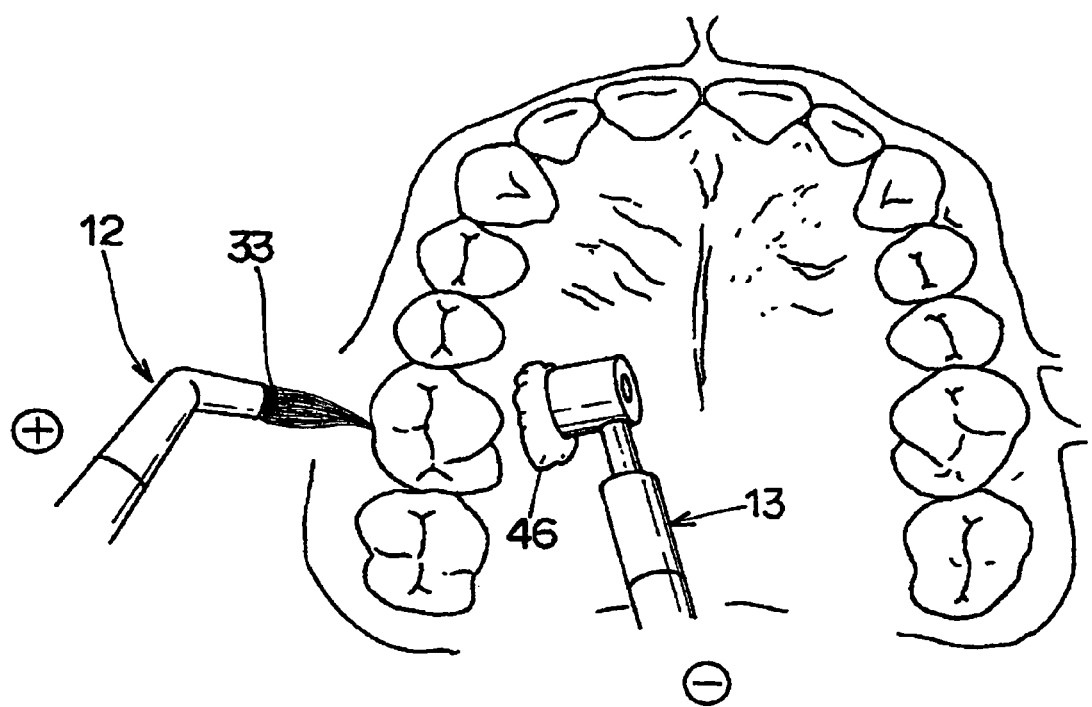
FIG. 5 is a plan view of a status of sterilization and treatment in the vicinity of a molar by the iontophoresis-based medical device according to one embodiment of the present invention.
Figure 6A:
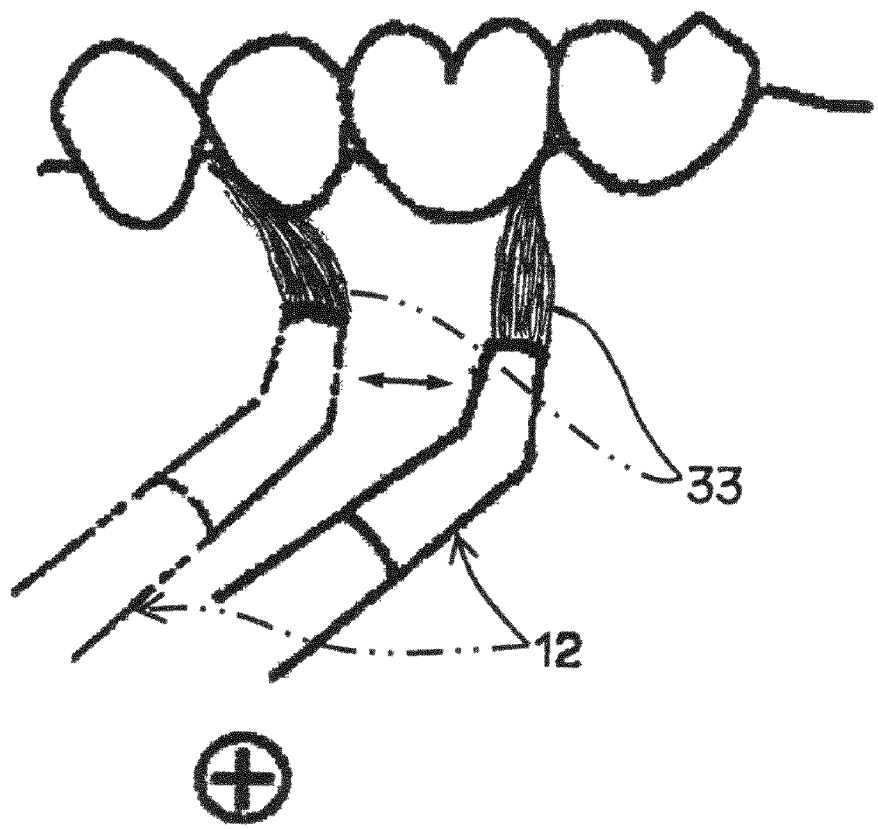
FIG. 6(a) is a side elevation view explaining how to use the positive electrode section in the vicinity of a molar.
Figure 6B:
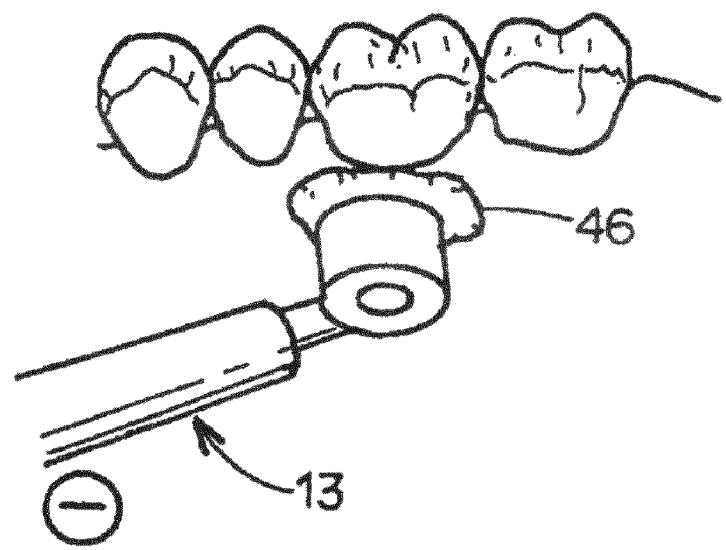
FIG. 6(b) is a side elevation view explaining how to use the negative electrode section in the vicinity of the molar.
Figure 7:
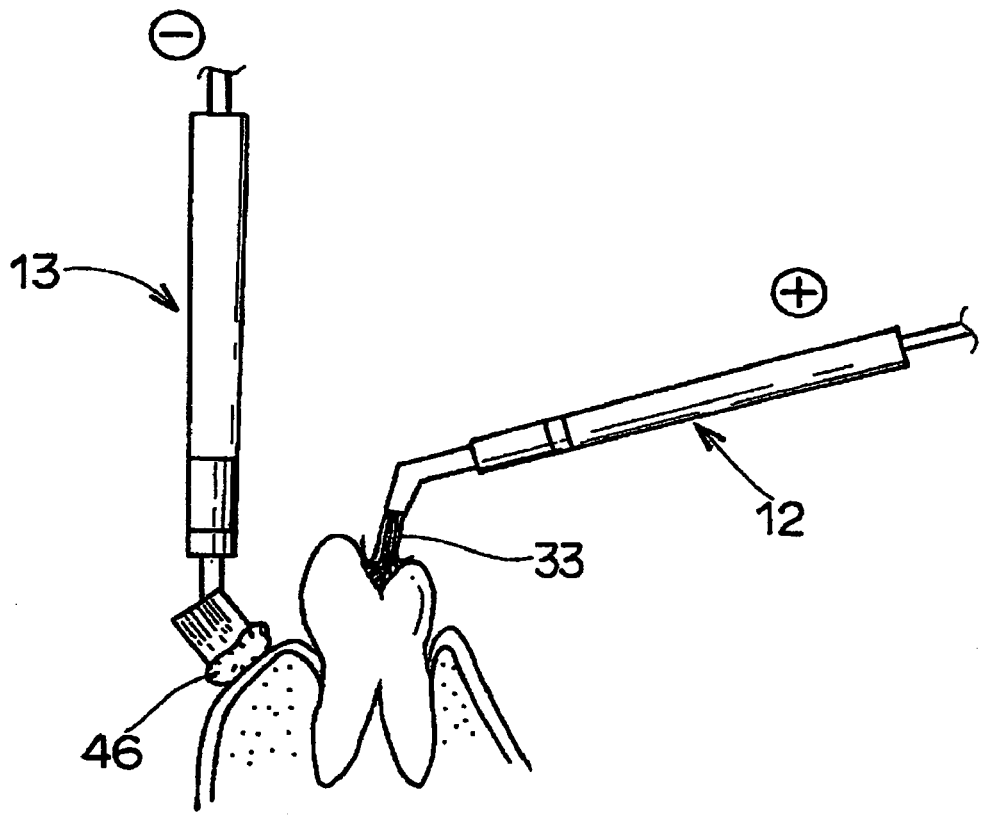
FIG. 7 is a sectional view showing a status of the sterilization and treatment of the molar by the iontophoresis-based medical device according to one embodiment of the present invention.
Figure 8:
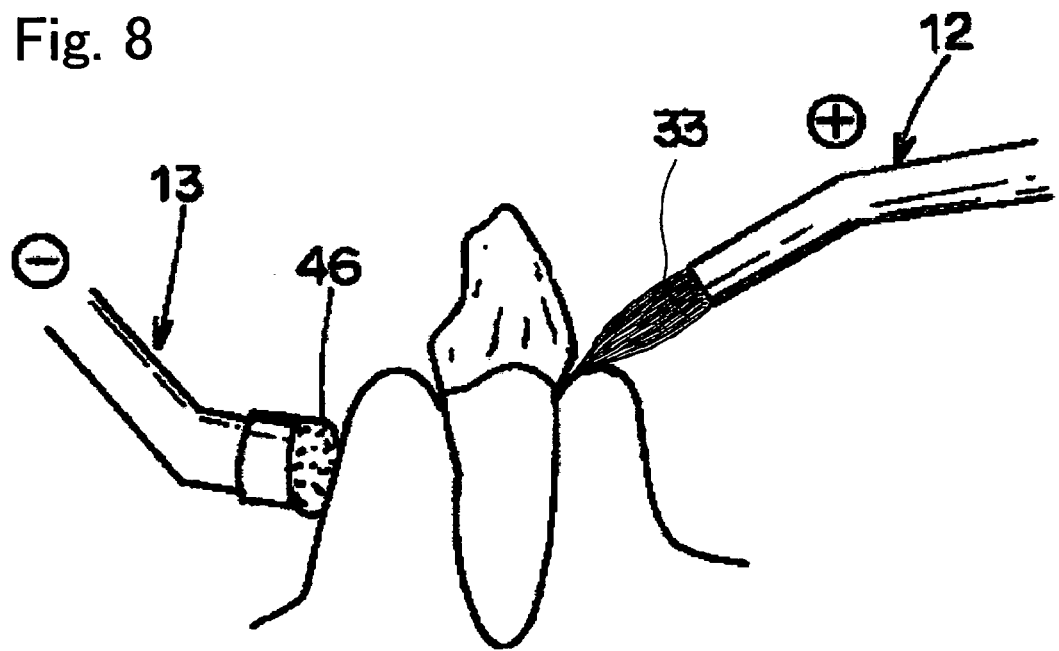
FIG. 8 is a sectional view showing a status of the sterilization and treatment of a front tooth by the iontophoresis-based medical device according to one embodiment of the present invention.

To explain the polarity inverting circuit 61 in more detail, the polarity inverting circuit 61 is electrically connected to a polarity inversion rate adjustment knob 60 which is arranged on a front surface portion of the device body 11. In supplying electricity to the inside of the oral cavity using the electrode sections 12, 13, the polarities of the positive and negative electrode sections 12, 13 are inverted at a time rate which is preliminarily set by a user as shown in FIG. 4(b). Here, in FIG. 4(a), a state where a voltage Va(V) is applied between both electrode sections 12, 13 using the positive electrode 12 as positive polarity and the negative electrode as negative polarity (also referred to as "positive application") is indicated by +Va(V), while a state where a voltage Va(V) is applied between both electrode sections 12, 13 using the positive electrode 12 as negative polarity and the negative electrode 13 as positive polarity (also referred to as "inverse application") is indicated by −Va(V). Further, FIG. 4(B) shows the behavior of the voltage applied between both electrode sections 12, 13 such that polarities are inverted at a time rate of 1 second for approximately 10 seconds.

The inversion of polarities is not particularly limited provided that the applying time of the inverse application during 1 cycle does not exceed the applying time of the positive application, and it is preferable to set the time rate becomes such that positive applying time: inverse applying time=10:1 to 5:1 in a state where the positive applying time is set to not less than 8 seconds.

When the inverse applying time assumes the time rate of less than 10:1, there exists a possibility that the foreign materials accumulated on the gingiva is not sufficiently removed. Further, there also exists a possibility that the penetration of the drug into the gingiva is impeded when the inverse applying time assumes the time rate which exceeds 10:1.

Next, an explanation will be made of the method for sterilizing and treating teeth or gingiva by using the iontophoresis-based medical device 10, with reference to FIG. 1 and FIG. 5 through FIG. 8.

First, 3% benzalkonium chloride aqueous solution is impregnated into the writing brush 33 and 3% sodium chloride aqueous solution is also impregnated into the sponge 46. Thereafter, the power switch 18 is turned on and the voltage adjusting knob 24 is turned to set the voltage to 1.5 to 2.0V. Further, the output switch 26 is turned to make an arbitrary selection, namely, sterilization and treatment by using continuous conduction or that by controlling the electric conduction time based on the buzzer 51 or controlling the conduction time based on the automatic on/off switch. In this instance, when the control based on the buzzer or electric conduction time is selected, the corresponding buzzer knob 25 or the electric conduction time knob 27 is turned to set a time until the buzzer 51 is sounded or intervals of switching from electric conduction to a lesion to discontinuation of the conduction.

Then, the writing brush 33 retaining benzalkonium chloride solution in the positive electrode section 12 is allowed to contact with a tooth or a part of the gingiva infected by a pathogen (FIG. 5, FIG. 6(a), FIG. 7 and FIG. 8). In addition, the sponge 46 to which sodium chloride aqueous solution of the negative electrode section 13 is impregnated is allowed to contact with the oral tissue in the vicinity of the above-mentioned infected tooth or gingiva (FIG. 5, FIG. 6(b), FIG. 7 and FIG. 8), thereby providing a closed electric circuit among the constant voltage circuit 49, current limiting circuit 53, positive and negative electrode sections 12 and 13, affected tooth, affected gingiva and oral tissue around the lesion. While maintaining this condition, the timer start switch 28 is turned on and a low current of 40 μA is conducted from the constant voltage circuit 49 through the current limiting circuit 53. Then, benzalkonium chloride is impregnated deeply into the tooth as ion through the action of iontophoresis. In this instance, a large quantity of benzalkonium chloride aqueous solution retained in the writing brush 33 is present in the positive electrode section 12 and a large quantity of sodium chloride aqueous solution retained in the sponge 46 is present in the negative electrode section 13, thereby offering a higher effect of iontophoresis than a device having the conventional needle-shaped electrode sections. Further, benzalkonium chloride is higher in an antimicrobial effect than conventional antimicrobial drugs such as halogen elements and metallic elements. Consequently, benzalkonium chloride can permeate deeply into a lesion and result in an effective sterilization of the tooth. The current value and electric conduction time should be appropriately determined, for example, in the respective ranges of 20 to 40 μA and 8 to 30 seconds, with consideration given to the position and condition of the target lesion.

Further, the polarities of both electrode portions 12, 13 can be inverted at a preset rate by operating the polarity inversion rate adjustment knob 60 so that it is possible to enhance a sterilizing effect while preventing the influence of foreign materials in the oral cavity as much as possible.

In addition to an antimicrobial effect derived from the iontophoresis action, an electric field is imparted to an aqueous solution to develop a bactericidal action directly from the electric field. Minute electrolytes contained in water, namely, positively charged ions such as $H_3O^+$ or $H_9O_4^+$ resulting from hydronium ions produced by electrolysis of sodium chloride and others, combine or collide with negative electric charge based on dissociation of phosphate groups existing on nucleotides of organisms or viruses to break nucleic acids, attaining an antimicrobial effect.

As explained above, since a large quantity of the benzalkonium chloride solution can be retained in the writing brush 33, it is possible to supply the drug solution to a lesion in a greater quantity than by a device provided with a positive electrode section having a conventional needle shape. Thus, the treatment time can be shortened and a lesion can be treated more effectively. Further, since the positive and negative electrode sections 12 and 13 are given a handleable shape, these electrode sections, 12 and 13, can be improved for handling at the time of treatment.

Further, since solutions used in iontophoresis include those in which benzalkonium chloride is contained as a major active ingredient, it is possible to give a potent antimicrobial effect to an affected tooth or an affected gingiva by utilizing iontophoresis at a lower cost.

In addition, controlling the current value and electric conduction time by the controller 47 makes it possible to provide treatment suitable to positions and conditions of the lesion.

According to the present invention, the writing brush is provided to the positive electrode section as a drug solution retainer capable of retaining a large quantity of a drug solution. That is, the writing brush is formed such that air pockets are formed among a large number of blended hairs so that the drug can be absorbed and stored through the capillarity and hence, compared to a positive electrode section having a conventional needle shape, it is possible to apply the drug to an affect part in a pinpoint manner, and at the same time, it is possible to apply the drug to the affected part while freely adjusting a supply quantity of the drug to the affected part.

Since the writing brush adopts the above-mentioned constitution, the treatment time can be shortened and, at the same time, the treatment effect of the affected part can be also enhanced.

Further, since the carbon fibers are mixed into the writing brush, it is possible to enhance the conductivity of electricity from the positive electrode section so that it is possible to perform the highly safe sterilizing treatment efficiently.

Controlling the current supplied to an electric circuit and electric conduction time in particular makes it possible to provide sterilization and treatment appropriate to the position and conditions of a lesion.

Further, by providing the polarity inverting circuit 61 to the electric circuit 15, it is possible to invert the polarities of voltages applied to the positive electrode connection terminal 19 and the negative electrode connection terminal 20 and hence, when the drug is inducted in the direction toward the gingiva from the positive electrode section 12 by means of iontophoresis, it is possible to remove the foreign materials which is induced to the gingiva and charged with a positive charge in the oral cavity.

That is, when the foreign materials which is charged with the positive charge and is contained in saliva or the like is induced to the negative electrode section 13 and is stacked on the gingiva during the penetration of the drug into the gingiva, the penetration of the drug gradually slows down thus hampering the effective treatment. According to the present invention, by inverting polarity of the voltage for a short time, the foreign materials stacked on the gingiva is induced to the positive electrode section 12 and the foreign materials is removed from the gingiva.

In addition, since the drug solutions in which a cationic surface active agent or amphoteric active agent is used as a main ingredient or amphoteric surface active agent is used as a main ingredient are used as drug solutions for treatment utilizing iontophoresis, it is possible to give a potent antimicrobial effect to lesion at a lower cost. Use of benzalkonium chloride or benzethonium chloride also provides other economic advantages.

The dimension and shape of the positive electrode section and the negative electrode section are not restricted as long as these can be handled. These are available, for example, as a stick with such a dimension and shape that can be held with one hand.

The drug solution is a solution in which a predetermined drug (medicine) is dissolved by water. The drug is not restricted to types, and, for example, halogen elements such as fluorine, iodine and chloride may be used. Metallic ions such as silver and zinc may also be used. In addition, a cationic surface active agent may be used.

Alternatively, other antimicrobial agents or antibiotics may be used as long as these are compounds (drugs) that can be dissolved in water and ionized as an ion.

No restrictions are given to methods for retaining a drug solution in the positive electrode section and those for retaining a solution in the negative electrode section. Further, such arrangement may be also acceptable where a large quantity of the drug solution or the solution is supplied to the positive electrode section and an excessive quantity of the drug solution or the solution is supplied to a lesion. In this instance, these solutions may be supplied continuously or intermittently.

The solution is not restricted to types, but preferable is a solution capable of increasing an electric conductivity. For example, sodium chloride solution (saline solution) potassium chloride solution, alum solution and calcium chloride solution may be used.

The drug solution retainer is not restricted to materials, shapes or dimensions, as long as the drug solution can be retained. The drug solution retainer is not restricted either to a site to be fixed on the positive electrode section, and can be fixed, for example, at the tip end of the positive electrode section.

The solution retainer is not restricted to materials, shapes or dimensions, as long as the solution can be retained. The solution retainer is not restricted to a site to be fixed on the negative electrode section either, and can be fixed, for example, at the tip end of the negative electrode section.

The power source may be a direct-current power source or an alternating current power source.

Upon electric conduction, the voltage value is to be 5V or lower, the current value is to be 40 μA or lower and the conduction time is to be 8 to 30 seconds. More particularly, in a case where dental pulp is sterilized and treated, for example, it is safe to apply a voltage value of less than 1.5V, a current value of less than 20 μA and an electric conduction time of less than 10 seconds. However, the current value and the conduction time should be determined, with consideration given to local conditions of the target site in the body.

An intensity of electric current is preferably 40 μA or lower, more preferably in a range from 20 to 40 μA. It is highly likely that an electric current exceeding 40 μA may cause drug-related damage (adverse effects) in the body. Further, an approximately constant current value corresponding to each target tissue makes it possible to control the action of drug solution ions only by adjusting the electric conduction time at subsequent processes. As a result, it is possible to treat a lesion in a simpler operation.

The electric conduction time is preferably 8 to 30 seconds and more preferably in a range from 15 to 30 seconds. A time of less than 8 seconds does not provide a sufficient therapeutic effect. Further, a time exceeding 30 seconds may result in development of damage to target tissues due to drug stimulation. However, in treating dental pulp, it is preferable to lessen the current value and the electric conduction time.

Further, the controller can be made up mainly with software by using a personal computer which is in the public domain, in addition to fabrication with electric circuits and elements mounted thereon.

The writing brush is not restricted to materials. For example, although the writing brush is made of the synthetic resin in the above-mentioned explanation, the writing brush may be made of animal hair and plant hair. The sponge is not restricted to materials either. For example, urethane resin, polyethylene and polypropylene may be adopted as the materials.

Further, the mouth piece is not restricted to configurations and can be formed as a shallow-bottom cylinder with an opening on one end, for example.

In the iontophoresis-based medical device having the above-mentioned constitution, the above-mentioned controller is able to set the current value, voltage value and electric conduction time on the above-mentioned electric conduction in response to the type of the target viscous membrane and thickness of the target skin and area of the target skin at the above-mentioned lesion.

The iontophoresis-based medical device having the above-mentioned constitution may include an alarm indicating the progress of the above-mentioned electric conduction time set by the above-mentioned controller.

An alarm (warning means) may include a buzzer and lighting.

In the iontophoresis-based medical device having the above-mentioned constitution, a main ingredient of the above-mentioned drug solution is a cationic surface active agent or an amphoteric surface active agent.

The cationic surface active agent includes, for example, benzalkonium chloride, benzethonium chloride, chlorhexidine gluconate and cation chloride cetylpyridinium, and the amphoteric surface active agent includes alkyldiaminoethylglycine hydrochloride.

Benzalkonium chloride is also known as alkyldimethylbenzylammonium salt and a sterilizing agent, which is aliphatic quaternary ammonium salt and available at a reasonable cost. This agent is listed in the Japanese Pharmacopoeia. It is a colorless or pale yellow aqueous solution and obtained by allowing alkyldimethylamine to react with benzylchloride.

Benzethonium chloride is also known as benzyldimethyl {2-[2-(p-1,1,3,3-tetramethylbutylphenoxy)etoxy]ethyl}ammonium chloride and a sterilizing agent listed in the Japanese Pharmacopoeia. This agent exhibits an antimicrobial activity against a wide range of bacteria and fungi, having a cleaning effect, keratolytic effect and emulsion effect.

In the iontophoresis-based medical device having the above-mentioned constitution, a 1 to 3% sodium chloride solution is impregnated into the above-mentioned sponge.

In the iontophoresis-based medical device having the above-mentioned constitution, the above-mentioned lesion is an oral lesion such as periodontal tissue, teeth, dental pulp or root canal or a superficial lesion on the body.

Dental disorders found as a lesion include periodontal disease, pulpitis and infected root canal.

Superficial lesions include skins which have developed candidiasis and ringworm.

In the iontophoresis-based medical device having the above-mentioned constitution, the above-mentioned current value is 40 μA or lower and the electric conduction time is 8 to 30 seconds when the above-mentioned lesion is an oral lesion in humans.

As explained above, since a large quantity of the drug solution can be retained in the drug solution retainer, it is possible to supply the drug solution to a lesion in a greater quantity than by a device provided with a positive electrode section having a conventional needle shape. Thus, the treatment time can be shortened and a lesion can be treated more effectively. Further, since the negative and positive electrode sections are given a stick shape comprised of a bar or a shaft having a predetermined length and thickness that can be handled, the electrode sections can be improved in handling at the time of treatment.

In addition to an antimicrobial effect derived from the iontophoresis action, an electric field is imparted to an aqueous solution to develop a bactericidal action directly from the electric field. Minute electrolytes contained in water combine or collide with a negative electric charge based on dissociation of phosphate groups existing on nucleotides of organisms or viruses, thus breaking nucleic acids to attain an antimicrobial effect. The minute electrolytes contained in water include positively charged ions such as $H_3O^+$ or $H_9O_4^+$ resulting from hydronium ions produced by electrolysis of sodium chloride or others.

Controlling the voltage supplied to an electric circuit, a current value and an electric conduction time in particular by the controller makes it possible to provide treatment suitable to positions and conditions of the lesion.

Further, the polarity inverting circuit is connected to the electric circuit so as to invert polarity of the voltage applied to the positive electrode connecting terminal to which the positive electrode section is connected and polarity of the voltage applied to the negative electrode connecting terminal to which the negative electrode section is connected at a predetermined time rate. Accordingly, by inverting the polarities of voltages for a short time occasionally, it is possible to induce the foreign materials stacked on the gingiva in the direction toward the positive polarity section thus removing the foreign material from the gingiva.

A cationic surface active agent and an amphoteric surface active agent are higher in an antimicrobial effect than a conventional drug such as halogen elements and metallic elements. Consequently, the lesion to which these surface active agents are permeated can be favorably sterilized.

Since drug solutions in which a cationic surface active agent or amphoteric surface active agent is used as a main ingredient are used as drug solutions for iontophoresis, it is possible to give a potent antimicrobial effect to a lesion by utilizing iontophoresis at a lower cost.

What is claimed is:

1. An iontophoresis-based medical device comprising:
   a device body having a positive electrode connecting terminal and a negative electrode connecting terminal;

a stick-shaped positive electrode section connected to the positive electrode connecting terminal and capable of retaining a drug solution in which an anti-microbial drug solution is dissolved therein;

a stick-shaped negative electrode section connected to the negative electrode connecting terminal and capable of retaining a solution increasing the conductivity therein; and an electric circuit connecting the positive electrode section and the negative electrode section respectively with a power source, wherein the device body has a rectangular device box on which the positive electrode connecting terminal, the negative electrode connecting terminal, a voltage adjusting knob, an output changeover switch for changing over continuous conduction and a timer control, an electric conduction time knob for changing an electric conduction time, and a timer start switch are mounted, the positive electrode section is connected to the positive electrode connecting terminal via a lead line, and the negative electrode section is connected to the negative electrode connecting terminal via a lead line, a writing brush is electrically connected to a distal end of the positive electrode section, and a sponge is electrically connected to a distal end of the negative electrode section, the writing brush is impregnated with an aqueous solution of a cationic surface active agent and the sponge is impregnated with a sodium chloride solution, the writing brush is formed of a large number of blended hairs consisting of a large number of long soft hairs and a large number of short soft hairs such that the writing brush has a columnar shape at a base portion thereof and is gradually tapered toward a tip portion thereof from a middle portion thereof and the tip portion is made extremely fine to form an acute apex thus allowing the apex to touch an affected part in a pinpoint manner, and the base portion of the writing brush formed of the blended hairs is made hard and the middle portion and the tip portion of the writing brush are made soft so that air pockets are formed in the large number of hairs so as to absorb and store a drug solution in the middle portion and the tip portion of the writing brush through capillarity, whereby conductivity of electricity to the writing brush at the positive electrode section is enhanced thus easily generating iontophoresis.

2. An iontophoresis-based medical device according to claim 1, further comprising:

a polarity inverting circuit connected to the electric circuit so as to invert polarity of a voltage applied to the positive electrode connecting terminal to which the positive electrode section is connected and polarity of a voltage applied to the negative electrode connecting terminal to which the negative electrode section is connected at a predetermined time rate; and a polarity inversion rate adjustment knob for adjusting a polarity inversion rate.

3. An iontophoresis-based medical device according to claims 1, 5 to 20% of the long soft hairs formed is formed of carbon fibers having the same diameter and the same length as the remaining long soft hairs.

* * * * *